United States Patent
Vercauteren et al.

(10) Patent No.: US 7,517,675 B2
(45) Date of Patent: Apr. 14, 2009

(54) OXIDATION OF CARBOHYDRATES BY MEANS OF PEROXIDASES AND NITROXY RADICALS

(75) Inventors: Ronny Leontina Marcel Vercauteren, Haasdonk (BE); An Amanda Jules Heylen, Zemst (BE)

(73) Assignee: Cerestar Holding B.V., Las Sas Van Gent (NL)

( * ) Notice: Subject to any disclaimer, the term of this patent is extended or adjusted under 35 U.S.C. 154(b) by 354 days.

(21) Appl. No.: 10/583,434

(22) PCT Filed: Dec. 17, 2004

(86) PCT No.: PCT/EP2004/014406

§ 371 (c)(1),
(2), (4) Date: Jun. 16, 2006

(87) PCT Pub. No.: WO2005/059152

PCT Pub. Date: Jun. 30, 2005

(65) Prior Publication Data

US 2007/0190619 A1    Aug. 16, 2007

(30) Foreign Application Priority Data

Dec. 18, 2003   (EP) ................. 03258025

(51) Int. Cl.
*C12P 7/58* (2006.01)
*C12P 7/40* (2006.01)
*C12P 19/02* (2006.01)
*C12P 19/04* (2006.01)
*C12P 7/24* (2006.01)

(52) U.S. Cl. ............... 435/136; 435/101; 435/104; 435/105; 435/137; 435/146; 435/147; 435/176; 435/177; 435/189; 435/192

(58) Field of Classification Search ............ None
See application file for complete search history.

(56) References Cited

U.S. PATENT DOCUMENTS

| 5,912,361 A | 6/1999 | Tsuchioka et al. |
| 7,138,035 B2 * | 11/2006 | Cui et al. ............... 162/175 |
| 2003/0029588 A1 | 2/2003 | Cui et al. |

FOREIGN PATENT DOCUMENTS

| EP | 1 077 221 | 3/2006 |
| WO | WO 96/36621 | 11/1996 |
| WO | WO 99/23240 | 5/1999 |
| WO | WO 00/50621 | 8/2000 |
| WO | WO 01/00681 | 1/2001 |

OTHER PUBLICATIONS

Chance and Maehly, "Assay of Catalases and Peroxidases," *Methods in Enzymology II*, 1955, pp. 764-775.
de Nooy et al., "Highly selective nitroxyl radical-mediated oxidation of primary alcohol groups in water-soluble glucans," *Carbohydrate Research*, 1995, 269(1):89-98.
Ibert et al., "Determination of the side-products formed during the nitroxide-mediated bleach oxidation of glucose to glucaric acid," *Carbohydrate Research*, 2002, 337(11):1059-1063.

* cited by examiner

*Primary Examiner*—Herbert J. Lilling
(74) *Attorney, Agent, or Firm*—Fish & Richardson P.C.

(57) ABSTRACT

A method of oxidising carbohydrates and/or carbohydrate derivatives having primary alcohol groups comprising contacting a reaction medium containing said carbohydrates and/or carbohydrate derivatives with a nitroxy radical mediator and a peroxidase enzyme, characterized in that the initial reaction medium contains at least 10% by weight carbohydrates and/or carbohydrate derivatives, in that the peroxidase enzyme is an oilseed peroxidase and in that a hydroperoxide and an alkali compound are gradually added to the reaction medium such that its pH is maintained at between 3.5 and 10.0 (pH-Stat); use of said method in a process for producing gluconic acid, glucaric acid and/or D-glucuronolactone.

27 Claims, No Drawings

OXIDATION OF CARBOHYDRATES BY MEANS OF PEROXIDASES AND NITROXY RADICALS

CROSS-REFERENCE TO RELATED APPLICATIONS

This application is a National Stage application under 35 U.S.C. §371 and claims benefit under 35 U.S.C. §119(a) of International Application No. PCT/EP2004/014406 having an International Filing Date of Dec. 17, 2004, which claims the benefit of priority of EP 03258025.0 having a filing date of Dec. 18, 2003.

TECHNICAL FIELD

The present invention relates to a process for the oxidation of carbohydrates and/or carbohydrate derivatives with a peroxidase enzyme and a nitroxy radical mediator. In particular, the present invention relates to the selective oxidation of primary alcohol groups to carboxyl groups.

BACKGROUND OF THE INVENTION

Oxidation of the primary alcohol groups of carbohydrates (and carbohydrate derivatives) leads to the formation of aldehyde (R'—CHO) and/or carboxyl (R'—COOH) groups.

The formation of aldehyde and carboxyl groups enhances the reactivity, versatility and solubility of the resulting compounds which, therefore, have a greater number of industrial applications (for example, in the food, textile and paper industries). As a result, there has been a great deal of interest in the development of methods allowing for the selective oxidation of primary alcohol groups. One such method involves the use of nitroxy radical mediators.

A number of nitroxy radical-mediated oxidation methods have been described in the art. Examples of such methods can be found in the following applications: WO00/50621A1, WO01/00681A1, US20030029588A1, and EP1077221A1.

Unfortunately, all of the existing methods have a number of disadvantages. Both US20030029588A1 and EP1077221A1, for example, require the use of environmentally hazardous halide compounds. The main drawback of existing methods, however, is their poor performance in terms of the quantity of carbohydrate substrate that can actually be oxidised at any one time. In both of WO00/50621A1 and WO01/00681A1, for instance, the amount of carbohydrate which can be added to the reaction mediums described is restricted to no more than 1 to 2% dry substance (more often than not, in fact, the dry substance levels do not exceed 0.05%).

Thus, for any useful quantity of oxidised carbohydrate to be obtained, very large amounts of reagent would be required and the amount of waste water produced would be considerable. It has been suggested, for example, that in order to increase oxidation levels, greater amounts of enzyme should be used. Not only would this undesirably increase reaction costs, but it has also been found to be ineffective. Accordingly, existing methods are neither economical, nor suitable for application on an industrial scale.

There exists, therefore, a need for an improved nitroxy radical-mediated oxidation process. The present invention provides such a process.

SUMMARY OF THE INVENTION

In a first aspect of the present invention, there is provided a method of oxidising carbohydrates and/or carbohydrate derivatives having at least one primary alcohol group comprising contacting a reaction medium containing said carbohydrates and/or carbohydrate derivatives with a nitroxy radical mediator and a peroxidase enzyme, characterised in that the initial reaction medium contains at least 10% by weight carbohydrates and/or carbohydrate derivatives, in that the peroxidase enzyme is an oilseed peroxidase and in that a hydroperoxide and an alkali compound (such as NaOH) are gradually added to the reaction medium such that its pH is maintained at between 3.5 and 10.0.

In a preferred embodiment, at least 10% of the primary alcohol groups are oxidised. Even more preferably, at least 50% of the oxidised primary alcohol groups are oxidised to carboxyl groups.

In a further aspect of the present invention, there is provided a process for producing gluconic and/or glucaric acid comprising oxidising glucose according to the above method.

In a yet further aspect of the present invention, there is provided a process for producing D-glucuronolactone comprising (a) oxidising trehalose according to the above method; (b) optionally recovering the nitroxy radical mediator; (c) hydrolysing the oxidised product of the reaction of step (a); (d) lactonising the product of the hydrolysation reaction of step (c) and (e) crystallising the product of step (d). Preferably, at least 15% of said trehalose is converted to D-glucuronolactone.

DETAILED DESCRIPTION

The present invention provides a method of oxidising carbohydrates and/or carbohydrate derivatives having at least one primary alcohol group comprising contacting a reaction medium containing said carbohydrates and/or carbohydrate derivatives with a nitroxy radical mediator and a peroxidase enzyme, characterised in that the initial reaction medium contains at least 10% by weight carbohydrates and/or carbohydrate derivatives, in that the peroxidase enzyme is an oilseed peroxidase and in that a hydroperoxide and an alkali compound are gradually added to the reaction medium such that its pH is maintained at between 3.5 and 10.0.

Carbohydrates and/or Carbohydrate Derivatives

The term "carbohydrate" refers to any compound containing at least one carbohydrate subunit. It may also comprise one or more non-carbohydrate subunits (e.g. lipid residues, protein residues and the like).

The at least one carbohydrate subunit may be a monosaccharide (such as glucose or fructose), a disaccharide (such as sucrose, maltose, lactose or trehalose) or an oligo- or polysaccharide (i.e. molecules having a degree of polymerisation of 3-10 and of more than 10, respectively).

The oligo- and polysaccharides may be of any type, including, but not limited to: galactans, (galacto)-mannans, furanofructans and xylans; α-glucans such as pullulan, starch, starch components (i.e. amylose or amylopectin) or starch derivatives (e.g. dextrins, maltodextrins or cyclodextrins); β-glucans such as cellulose or chitin; fructans such as inulin; natural or artificial gums such as xanthan, guar, gum arabic, agar, carrageenan, and the like.

The method of the present invention may also be used to oxidise derivatives and/or salts of any of the above carbohydrates. For ease of reference, such compounds will be termed "carbohydrate derivatives". Derivatives include chemically, enzymatically and/or thermally modified carbohydrate compounds. Examples of preferred carbohydrate derivatives suitable for use in the method of the invention include, but are not limited to, reduced carbohydrates (such as glycerol, sorbitol, mannitol, xylitol, lactitol, maltitol, erythritol glycerol, threitol, arabinitol, ribitol, isomalt and isomaltitol), amino-carbohydrates, glyconamides, glycosylamines, nitrogenous carbohydrate derivatives, deoxy-carbohydrates, thio-carbohydrates, thio-reduced carbohydrates, unsaturated carbohydrates, anhydro-derivatives of carbohydrates, anhydro-derivatives of reduced carbohydrates, carbohydrate glycosides, carbohydrate ethers, carbohydrate ethers and carbohydrate esters (including carboxylic, sulphonate, phosphate, borate, nitrate, sulphate, carbonate, thiocarbonate and carbamate esters).

Preferably, the carbohydrate or carbohydrate derivative will be selected from starch, glucose, trehalose, malto-oligosaccharides, isomalto-oligosaccharides, glucose syrups, maltodextrin, glycerol and sorbitol, or a mixture of two or more thereof.

Reaction Medium

At least 10%, preferably at least 20%, more preferably at least 30%, even more preferably at least 40%, by weight dry substance of the carbohydrate and/or carbohydrate derivative is added to the initial reaction medium, wherein "initial" reaction medium refers to the reaction medium before the oxidation reaction is started.

The reaction medium can be an aqueous medium, a homogeneously mixed medium (e.g. an alcohol/water or an ether/water mixture) or a heterogeneous medium (e.g. a mixture of water and a water-immiscible organic solvent such as a hydrophobic ether, a hydrocarbon or a halogenated hydrocarbon).

According to a preferred embodiment, the reaction medium may also be a solid/liquid mixture wherein the nitroxy radical mediator and/or the peroxidase enzyme of the present invention are immobilised on an inert support. The mediator and/or enzyme can be immobilised using any method known in the art (e.g. chemical covalent bonding, gel entrapment, adsorption, encapsulation onto a semi-permeable membrane, crosslinking and the like).

Nitroxy Radical Mediator

Irrespective of its form, the initial reaction medium will advantageously comprise a molar ratio of nitroxy radical mediators to primary alcohol groups of 1:4 to 1:150, preferably a ratio of about 1:40 to 1:70. The nitroxy radical mediator may be, by way of example only, a di-tert-nitroxyl compound such as 2,2,6,6-tetramethylpiperidine-N-oxyl (TEMPO), an organic nitroxyl compound lacking a-hydrogen atoms such as 2,2,5,5-tetramethylpyrrolidine-N-oxyl (PROXYL), 4-hydroxy, 4-methoxy, 4-alkoxyl, 4-acetoxy, 4-phosphonooxy or 4-benzoyloxy-TEMPO, acylated derivatives thereof such as 4-acetamido- and 4-maleimido-TEMPO or dehydro-TEMPO (1,2,3,6-tetrahydro-2,2,6,6-tetramethylpyridin-1-oxyl).
Preferably, the nitroxy radical mediator will be TEMPO or 4-methoxy TEMPO.

The active oxidising species of nitroxy radical mediators is the nitrosonium ion ($>N^+=O$) and the term "nitroxy radical mediator" is intended to refer to both activated and inactive forms of a nitroxyl compound. Activated nitroxy radical mediators may be added directly to the reaction medium but are preferably produced in situ by oxidation.

The nitroxy radical mediator may also be a derivative or analogue of any of the above or a combination of two or more thereof. Ideally, after use, the nitroxy radical mediator will be recovered and recycled to the reaction medium using any known method (the method described in WO96/36621A1, for example).

Peroxidase Enzyme

Peroxidase enzymes will be added to the initial reaction medium, preferably in an amount of 2000 to 540,000 units per mole of primary alcohol, more preferably in an amount of approximately 5000 units per mole of primary alcohol. Peroxidase enzyme units can be determined using standard methods in the art such as that set out in Chance, B. and Maehly, A. C. (1955) Methods in Enzymology II, pages 773-775.

The peroxidase enzyme used in the method of the present invention is an oilseed-derived peroxidase enzyme, preferably selected from the enzyme classification EC 1.11.1, more preferably from EC 1.11.1.7. Suitable sources for such enzymes include, but are not limited to, soybean, rapeseed, safflower, sunflower, flax, cotton, mustard, crambe (or other plants of the Brassica genus) oil palm and grouidnuts. Preferably, the peroxidase enzyme will be soybean or oil palm peroxidase.

pH Control

The use of peroxidase enzymes requires the presence of an electron acceptor. The electron acceptor used in the present method will be a hydroperoxide. The hydroperoxide will preferably be hydrogen peroxide or a source thereof, e.g. a hydrogen peroxide precursor such as perborate or percarbonate; a hydrogen peroxide generating enzyme; peroxycarboxylic acid or a salt thereof. For each mole of primary alcohol, 0.5 to 4 mmol/min hydroperoxide will be added to the reaction medium. Its addition should be slow and controlled such that the pH of the reaction medium can be maintained at between 3.5 and 10.0.

The optimum pH of the reaction medium will, to a certain extent, depend on the substrate to be oxidised. Thus, for most carbohydrates, and in particular for trehalose, the preferred pH will be between 3.5 and 8.0. More preferably, it will be between 4.0 and 7.5, even more preferably approximately 7. However, for certain carbohydrate derivatives (such as reduced carbohydrates and glycerol in particular), the preferred pH will be between 5.0 and 10.0.

In addition to a hydroperoxide, the pH of the reaction medium is further maintained by the gradual addition of an alkali compound. Thus, for each primary alcohol group, 0.1 to 1.1 mmol/min alkali compound is added to the reaction medium. The alkali compound is preferably sodium hydroxide (NaOH). The addition of the hydroperoxide and alkali compound is controlled using a pH stat.

In addition to the pH of the reaction medium, its temperature is ideally also controlled. Thus, the reaction medium will preferably be maintained at between 15 and 50° C., preferably at between 20 and 30° C., even more preferably at approximately 25° C. According to one embodiment, reaction time may be as little as 20 hours. According to another embodiment, it may be up to or more than 100 hours. Preferably, however, it will be from 40 to 55 hours, even more preferably from 45 to 52 hours.

Under the reaction conditions described above, it has surprisingly been found that high levels of carbohydrate (and/or carbohydrate derivative) dry substance can be included in the initial reaction medium. In particular, it has been found that 10% or more, preferably at least 20%, more preferably at least 30%, more preferably at least 40%, more preferably at least 50%, more preferably at least 60%, more preferably at least 70%, more preferably at least 80%, even more preferably at least 90%, of the primary alcohol groups present in the initial reaction medium will be oxidised. According to a preferred embodiment, the oxidised primary alcohol groups will be oxidised to carboxyl groups. According to an especially preferred embodiment, at least 50% of the oxidised primary alcohol groups will be oxidised to carboxyl groups. Ideally, at least 90% of the oxidised primary alcohol groups will be oxidised to carboxyl groups.

Production of Gluconic and/or Glucaric Acid

The actual product of the oxidation reaction will of course depend on the carbohydrate and/or carbohydrate derivative used as substrate. In one possible embodiment, wherein the carbohydrates added to the initial reaction medium is glucose, the product of the reaction will be gluconic acid (C1 oxidation) or glucaric acid (C1 and C6 oxidation). Thus, the present invention provides a process for producing gluconic or glucaric acid by oxidising glucose.

Production of D-Glucuronolactone

The products of the present oxidation reaction can further be modified e.g. by additional oxidation, hydroxyalkylation, carboxymethylation, cationisation, amidation, esterification, crosslinking or by hydrolysis.

Thus, for example, the present invention provides a process for producing D-glucuronolactone comprising (a) oxidising trehalose according to the above-described method, (b) optionally recovering the nitroxy radical mediator; (c) hydrolysing the oxidised product of the reaction of step (a); (d) lactonising the product of the hydrolysation reaction of step (c) and (e) crystallising the product of step (d). Preferably, at least 15% of said trehalose will be converted to D-glucuronolactone.

Trehalose is a non-reducing disaccharide comprising D-glucose as a constituent sugar. It can be extracted from plants, bacteria, fungi, algae or insects or it may be derived, for example, from maltose or starch. Oxidized trehalose can be hydrolysed by reacting it with one or more hydrolyzers selected from acids such as hydrochloric acid, nitric acid, phosphoric acid, sulphuric acid, super-acids and/or a cation exchange resin.

Even more preferably, the oxidised trehalose will be enzymatically hydrolysed. Suitable hydrolase enzymes include, but are not limited to, O-glycosyl compound hydrolysing enzymes such as galacturonase enzymes. Preferably, the hydrolase enzyme will be exo-polygalacturonase. The enzyme will be added to the reaction medium in amounts of 0.05-30% w/w, preferably 2-20% w/w. The enzyme may be free in solution or it may be immobilised on an inert support using any known method.

Hydrolysis will preferably be carried out in a liquid phase such as water, a solvent such as straight-chain or branched lower alcohols (e.g. methanol, ethanol, butanol propanol and isopropyl alcohol) or a mixture of two or more thereof. Reaction times can vary from 1 to 150 hours, preferably 5 to 80 hours, even more preferably 5 to 10 hours. The pH will preferably be maintained at between 3 and 6, even more preferably between about 4 and 5 such that the hydrolysed glucuronate product may be acidified to glucuronic acid. Incubation temperature can be set to 30-50° C., preferably about 40° C.

The lactonisation step is used to convert glucuronic acid to glucuronolactone (e.g. with an acid such as hydrochloric acid, sulphuric acid, nitric acid or phosphoric acid). D-glucuronolactone can then be separated from the reaction product by crystallisation followed by any one or more of the following processes: filtration, extraction, solid-liquid separation, fractional precipitation, dialysis distillation and so forth. If D-glucuronolactone of higher purity is required, techniques commonly used in the art for purifying sugars or sugar derivatives may be applied as exemplified by thin-layer chromatography, column chromatography, ion-exchange chromatography, gas chromatography, distillation and crystallization. D-glucuronolactone produced according to the method of the present invention can be used, for example, in nutritional compositions, in energy foods or drinks and in pharmaceutical products.

The invention will now be further illustrated by way of non-limiting examples.

EXAMPLES

Example 1

Production of Gluconic and Glucaric Acid 15 g of D-glucose (from Aldrich) were dissolved in 21.5 ml demineralised water (=39.9% dry substance). 1.056 g of TEMPO (from Aldrich) were added to the glucose solution. 0.0206 g of soybean peroxidase (SIGMA™) were added and the reaction was allowed to stir for 24 h at 25° C. Hydrogen peroxide (30% Perhydrol™ from Merck) was continuously added at a dose rate of 0.138 mmol/min. The pH was kept constant at 7 by addition of 4 M NaOH (from Merck).

After 24 h, the reaction mixture was analysed by HPLC. Samples were analysed at 75° C. and at 1 ml/min on two separate columns: a Shodex K-S-801 ($Na^+$ form) column with water and a Shodex KC-811 ($H^+$ form) column with 0.01 M $H_2SO_2$. The two chromatograms obtained were used to determine the levels of glucuronic acid (4.4%), gluconic acid (86.5%) and glucaric acid (6.8%) produced by the oxidation reaction.

Example 2

Determination of Aldehyde Content in Oxidised Trehalose (Trial 1)

Oxidation Procedure

The selective C6-oxidation of 20 g D-trehalose (ASCEND™ from Cargill) was performed in lab trials with soybean peroxidase/hydrogen peroxide and TEMPO (from Aldrich) as mediator. The following conditions were used:

dry substance D-trehalose : 40% d.s.

molar ratio TEMPO/primary alcohol function*: 1/40

*The primary alcohol function referred to above has the chemical formula —$CH_2$—OH but can be abbreviated to "primary OH".

soybean peroxidase (OrganicTec™): 10 000 Units/mol primary OH hydrogen peroxide (30% Perhydrol™): 0.01 ml/min sodium hydroxide 4 M solution for pH stat control at pH 7 reaction temperature: 25° C.

The reaction medium was continuously agitated with a magnetic stirrer. Samples were taken after increasing reaction times (10, 21, 28 and 36 h) corresponding to a sodium hydroxide consumption of 17, 42, 60 and 74 mol % NaOH/primary OH, this being a measure for degree of oxidation.

Aldehyde Determination

The hydroxylamine hydrochloride titration with sodium hydroxide was based on the method described in patent EP1 077 221 A1 ("Polysaccharide aldehydes prepared by oxidation method and used as strength additives in papermaking").

The pH of a sample containing 15 mmol primary OH was adjusted to pH 3.2 with 1 M HCl, i.e. the pH at the equivalent point of HCl.

An excess of hydroxylamine hydrochloride was added (1.5 M solution from Merck).

Via oxime derivatisation according to the described reaction mechanism, HCl was formed and by means of a Metrohm pH Stat 718 Titrino, 0.1 M NaOH was added in order to maintain the pH value at 3.2. The amount of NaOH moles added was a measure for the number of aldehyde groups present.

reaction mechanism: R—CHO+NH$_2$OH.HCl−>RCH-NOH+HCl

The determination results are given in Table 1, below.

TABLE 1

| Aldehyde determination | | |
|---|---|---|
| oxidation reaction time (h) | uronic acid/primary OH (mol %) | aldehyde/primary OH (mol %) |
| 10 | 17 | 13 |
| 21 | 42 | 10 |
| 28 | 60 | 6 |
| 36 | 74 | 5 |

The primary OH of D-trehalose was oxidised to aldehyde prior to the formation of carboxylic acid. The aldehyde determination at different degrees of oxidation showed lower values of aldehyde at higher oxidation degrees. The aldehyde content corresponding with oxidation degrees of 17, 42, 60 and 74 mol % uronic acid/primary OH was respectively 13, 10, 6 and 5 mol % aldehyde/primary OH.

Example 3

Determination of Aldehyde Content in Oxidised Trehalose (Trial 2)

Oxidation Procedure

The selective C6-oxidation of 20 g D-trehalose was performed in lab trials with soybean peroxidase/hydrogen peroxide and TEMPO (from Aldrich) as mediator. The following conditions were used:

dry substance D-trehalose : 40% d.s.

molar ratio TEMPO/primary OH: 1/40 soybean peroxidase (OrganicTec™): 5000 Units/mol primary OH hydrogen peroxide (30% Perhydrol™): 0.01 ml/min sodium hydroxide 4 M solution for pH stat control at pH 5, pH 6, pH 7 and pH 8 reaction temperature: 25° C.

Samples were taken after increasing reaction times. The corresponding sodium hydroxide consumptions are shown in Table 2.

Carboxyl Group and Aldehyde Determination

In addition to NaOH consumption, the standard Blumenkrantz (specific uronic acid quantification) and HPLC methods were used to determine levels of oxidation. HPLC was run at 25° C. and at 1 ml/min on two consecutive Shodex KC-811 (H$^+$ form) columns with 0.01 M H$_2$SO$_2$.

Aldehyde levels were determined using the method described in Example 2 above.

The results obtained are set out in Table 2.

TABLE 2

| Oxidation reaction | Oxidation (%) | | | Aldehyde |
|---|---|---|---|---|
| time (h) | (HPLC) | (NaOH cons.) | (Blumenkrantz) | (%) |
| pH 5  10 | 30 | 20 | 23 | 12.8 |
| 28 | 71 | 67 | 70 | 7.4 |
| 52 | 95 | 93 | 94 | 4.7 |
| pH 6  28 | 28 | 18 | 20 | 13.2 |
| 10 | 67 | 60 | 66 | 7.3 |
| 48 | 98 | 96 | 99 | 3.7 |
| pH 7  10 | 29 | 19 | 23 | 11.0 |
| 28 | 63 | 58 | 58 | 8.9 |
| pH 8  21 | 21 | 19 | 16 | 7.8 |

The primary OH of D-trehalose was oxidised to aldehyde prior to the formation of carboxylic acid. The aldehyde determination at different degrees of oxidation showed lower values of aldehyde at higher oxidation degrees.

Example 4

Oxidation of Trehalose without pH Control (Comparative Example)

Trehalose oxidation was performed in lab trials with soybean peroxidase/hydrogen peroxide and TEMPO (from Aldrich) as mediator. The following conditions were used;

dry substance D-trehalose : 40% d.s.

molar ratio TEMPO/primary OH: 1/70 soybean peroxidase (OrganicTec™): 5000 Units/mol primary OH hydrogen peroxide (30% Perhydrol™): 2.4 mol/mol primary OH, dosed over 52 hours reaction temperature: 25° C.

Without pH control, it was found that only 9% of the trehalose was oxidised, with 83% trehalose remaining in solution.

Example 5

Oxidation with Non-Oilseed Peroxidase (Comparative Example)

To a 20 g trehalose solution at 40% ds, TEMPO (from Aldrich) was added in a molar ratio TEMPO/primary OH of 1/40. As peroxidase, horseradish peroxidase (from Fluka) was used at a dosage of 10000 U/mol primary OH.

The oxidation was carried out at 25° C. Hydrogen peroxide (30% Perhydrol™) was added at a flow rate of 0.01 ml/min. The pH was maintained at pH 7 by addition of NaOH 4 M. After 1 h of reaction, the hydrogen peroxide concentration exceeded 25 ppm. The reaction was continued up to 49 h, with a total of 29.3 ml hydrogen peroxide addition and a NaOH consumption of 0.6 ml. HPLC analysis showed 0.7% oxidation. Thus, no significant oxidation is achieved if horseradish peroxidase is used.

The invention claimed is

1. A method of oxidising carbohydrates and/or carbohydrate derivatives having at least one primary alcohol group comprising contacting a reaction medium containing said carbohydrates and/or carbohydrate derivatives with a nitroxy radical mediator and a peroxidase enzyme, wherein the reaction medium contains at least 10% by weight carbohydrates and/or carbohydrate derivatives, wherein the peroxidase enzyme is an oilseed peroxidase, and wherein a hydroperoxide and an alkali compound are gradually added to the reaction medium such that its pH is maintained at between 3.5 and 10.0.

2. A method according to claim 1, wherein the carbohydrates and/or carbohydrate derivatives are selected from the group consisting of starch, glucose, trehalose, maltooligosaccharides, isomalto-oligosaccharides, glucose syrups, maltodextrins, glycerol, sorbitol, and mixtures thereof.

3. A method according to claim 1, wherein the pH is maintained between 3.5 and 8.0.

4. A method according to claim 1, wherein the pH is maintained between 5.0 and 10.0.

5. A method according to claim 1, wherein the reaction medium contains at least 40% by weight carbohydrates and/or carbohydrate derivatives.

6. A method according to claim 1, wherein at least 10% of the primary alcohol groups are oxidised.

7. A method according to claim 6, wherein at least 50% of the oxidised primary alcohol groups are oxidised to carboxyl groups.

8. A method according to claim 1, wherein the nitroxy radical mediator is a di-tert-nitroxyl compound.

9. A method according to claim 1, wherein the reaction medium comprises a molar ratio of nitroxy radical mediators to primary alcohol groups of 1:4 to 1:150.

10. A method according to claim 1, wherein the peroxidase enzyme is selected from the group consisting of: rapeseed peroxidase, palm oil peroxidase, groundnut peroxidase, soybean peroxidase and mixtures thereof.

11. A method according to claim 1, wherein the peroxidase enzyme is soybean or palm oil peroxidase.

12. A method according to claim 1, wherein the reaction medium comprises 2000 to 540 000 Units of peroxidase enzyme, per mole of primary alcohol.

13. A method according to claim 1, wherein the peroxidase enzyme is immobilised on a support.

14. A method according to claim 1, wherein, for each mole primary alcohol, 0.5 to 4 mmol/min hydroperoxide are added to the reaction medium.

15. A method according to claim 1, wherein the hydroperoxide is hydrogen peroxide or a source thereof.

16. A method according to claim 1, wherein, for each primary alcohol group, 0.1 to 1.1 mmol/min alkali compound is added to the reaction medium.

17. A method according to claim 1, wherein the alkali compound is sodium hydroxide.

18. A method according to claim 1, wherein the reaction medium is maintained at a temperature of between 20 and 50° C.

19. A method according to claim 1, wherein the reaction time is from 20 to 55 hours.

20. A process for producing gluconic and/or glucaric acid comprising oxidising glucose according to the method of claim 1.

21. A process for producing oxidised trehalose comprising oxidising trehalose according to the method of claim 1.

22. A method according to claim 1, wherein the pH is maintained between 4.0 and 7.5.

23. A method according to claim 8, wherein the nitroxy radical mediator is 2,2,6,6-tetramethylpiperidin-1-oxyl (TEMPO) or derivatives or mixtures thereof.

24. A method according to claim 1, wherein the reaction medium comprises a molar ratio of nitroxy radical mediators to primary alcohol groups of 1:40 to 1:70.

25. A method according to claim 1, wherein the reaction medium comprises approximately 5000 Units of peroxidase enzyme per mole of primary alcohol.

26. A method according to claim 1, wherein the reaction medium is maintained at a temperature at about 25° C.

27. A method according to claim 1, wherein the reaction time is from 45 to 52 hours.

* * * * *

UNITED STATES PATENT AND TRADEMARK OFFICE
CERTIFICATE OF CORRECTION

| | | |
|---|---|---|
| PATENT NO. | : 7,517,675 B2 | Page 1 of 1 |
| APPLICATION NO. | : 10/583434 | |
| DATED | : April 14, 2009 | |
| INVENTOR(S) | : Ronny Leontina Marcel Vercauteren | |

It is certified that error appears in the above-identified patent and that said Letters Patent is hereby corrected as shown below:

Column 9, line 35 (Claim 12), please delete "enzyme," and insert --enzyme-- therefor.

Signed and Sealed this

Fourteenth Day of July, 2009

JOHN DOLL
*Acting Director of the United States Patent and Trademark Office*